United States Patent [19]

Byrne et al.

[11] Patent Number: 5,601,535
[45] Date of Patent: Feb. 11, 1997

[54] SAFETY DEVICE FOR HYPODERMIC NEEDLE OR THE LIKE

[75] Inventors: Phillip O. Byrne; Penelope R. Sisson; Harry R. Ingham, all of Newcastle upon Tyne, England

[73] Assignee: British Technology Group Ltd., London, England

[21] Appl. No.: 160,859

[22] Filed: Dec. 3, 1993

Related U.S. Application Data

[63] Continuation of Ser. No. 709,999, Jun. 4, 1991, which is a continuation of Ser. No. 595,664, Oct. 11, 1990, Pat. No. 5,084,030, which is a continuation of Ser. No. 241,256, Sep. 7, 1988, abandoned, which is a continuation of Ser. No. 888,376, Jul. 23, 1986, Pat. No. 4,826,490.

[30] Foreign Application Priority Data

Jul. 29, 1985 [GB] United Kingdom ............ 8509149

[51] Int. Cl.$^6$ ........................................ A61M 5/32
[52] U.S. Cl. .................. 604/198; 604/110; 604/263
[58] Field of Search .................. 604/110, 192, 604/198, 263

[56] References Cited

U.S. PATENT DOCUMENTS

| | | |
|---|---|---|
| 2,876,770 | 10/1955 | White . |
| 2,925,083 | 12/1957 | Craig . |
| 3,323,523 | 6/1967 | Scislowicz et al. ............ 604/162 |
| 3,463,152 | 8/1969 | Sorenson . |
| 3,536,073 | 10/1970 | Farb ............ 604/162 |
| 3,574,306 | 4/1971 | Alden ............ 604/162 |
| 3,610,240 | 10/1971 | Harautuneian ............ 604/162 |
| 3,658,061 | 4/1972 | Hall ............ 604/263 |
| 3,884,230 | 5/1975 | Wulff . |
| 3,890,971 | 6/1975 | Leeson et al. ............ 604/198 X |
| 3,904,033 | 9/1975 | Haerr . |
| 4,170,993 | 10/1979 | Alvarez ............ 604/180 |
| 4,425,120 | 1/1984 | Sampson et al. ............ 604/198 |
| 4,573,976 | 3/1986 | Sampson et al. ............ 604/198 |
| 4,631,057 | 12/1986 | Mitchell ............ 604/198 |
| 4,664,259 | 5/1987 | Landis ............ 206/365 |
| 4,666,435 | 5/1987 | Bragintez ............ 604/198 |
| 4,693,257 | 9/1987 | Markham ............ 604/198 X |
| 4,695,274 | 9/1987 | Fox ............ 604/198 |
| 4,743,233 | 5/1988 | Schneider ............ 604/192 |
| 4,931,048 | 6/1990 | Lopez et al. . |

FOREIGN PATENT DOCUMENTS

| | | |
|---|---|---|
| 813433 | 7/1951 | Germany . |
| 49-4797 | 2/1974 | Japan . |
| 924734 | 5/1963 | United Kingdom . |
| 1233302 | 5/1971 | United Kingdom . |
| 1297746 | 11/1972 | United Kingdom . |
| 2059268 | 4/1981 | United Kingdom . |
| 2114006 | 8/1983 | United Kingdom . |

*Primary Examiner*—Corrine M. McDermott
*Attorney, Agent, or Firm*—Cushman Darby & Cushman IP Group of Pillsbury Madison & Sutro LLP

[57] ABSTRACT

A safety device for a hypodermic needle or for a similar instrument used in the clinical puncture of the skin comprises a sheath (6, 25 or 32) adapted to be connected to the needle (5, 21 or 33) or to a support (4 or 31) for the needle. The sheath is so connected in a first position (FIG. 1A, 2A, or 3A) which permits normal use of the needle and can be placed, by movement relative to the needle (FIG. 1B or 3B) or by folding upon itself (FIGS. 2B and 2C) in a second position in which the needle is encapsulated by the sheath. The sheath is retained in that second position, for example by a projection (9, 27 or 35) extending into a slot (10 or 36) or through an aperture (28).

20 Claims, 3 Drawing Sheets

SAFETY DEVICE FOR HYPODERMIC NEEDLE OR THE LIKE

This is a continuation of application Ser. No. 07/709,999 filed Jun. 4, 1991 pending which is a continuation of Ser. No. 07/595,664 filed Oct. 11, 1990 (now U.S. Pat. No. 5,084,030), which is a continuation of Ser. No. 07/241,256 filed Sep. 7, 1988 (now abandoned), which is a continuation of Ser. No. 06/888,376 filed Jul. 23, 1986 (now U.S. Pat. No. 4,826,490).

The present invention is a safety device for a hypodermic needle or similar instrument used in the clinical puncture of the skin.

The taking of blood samples from persons in hospitals, health centres or other clinical areas is a routine medical procedure, as is the injection of pharmaceutical preparations or biological materials. However, many incidents have been reported in the press and in medical journals of clinical operators subsequently accidentally wounding themselves or other persons with the needle and thereby either transmitting a disease or causing chemical or biological poisoning.

There is a clear need for a device which permits the disposal of a hypodermic needle or such instrument in a manner which protects the clinical operator, observers of the clinical procedure and all other persons concerned, including the general public, from accidental wounding.

It is an object of the present invention to provide such a device.

The safety device according to the invention for a hypodermic needle or similar instrument comprises a sheath, adapted to be connected to said needle or other instrument or to a support therefor in a first position which permits normal use of said needle or other instrument and to be placeable, by movement relative to the needle or other instrument or by folding upon itself, in a second position in which the needle or other instrument is encapsulated by the sheath and the sheath is retained in that second position.

As indicated, the safety device of the present invention is generally applicable to the protection of puncturing instruments typified by hypodermic needles, although among such instruments hypodermic needles are by far the most widely used. For example, the device may be applied to the protection of biopsy needles, winged needles, that is needles provided with lateral attachments to enable them to be affixed to the skin surface as by adhesive tape, and to intravenous cannulas and lumbar puncture needles. For convenience, the invention is hereinafter described specifically as applied to "needles", in particular hypodermic needles, but it is emphasised that the invention is not to be limited thereby.

The sheath is adapted to be attached to the needle or to a support for the needle but may be provided separately from the needle, to be attached to the needle or support at the point of use, either before or after the needle has actually been used. It is much preferred that such separate sheaths be attached before use, so that the needle may be more readily encapsulated immediately after it has been used. However, the sheath according to the present invention is preferably and conveniently supplied already attached to the needle. In particular, it is preferably attached either irremovably or in a way which makes its removal difficult. For example, the sheath may be adhered to the needle or to a support for the needle or may be clipped to the needle or support.

When the needle is designed for use without a syringe or remote from an associated syringe, to which it is then linked by a flexible tube, then the sheath is preferably secured direct to the needle. The sheath may then conveniently incorporate one or more parts which are foldable relative to the body of the sheath and thereby to encapsulate the needle.

When the needle, on the other hand, is mounted upon a housing designed to be attached to a syringe barrel or luer connector, then the sheath may advantageously be secured to the housing. The sheath may then be capable of movement relative to the housing in a direction which has a component parallel to the length of the needle, so that the sheath may be moved along the length of the needle until the latter is fully encapsulated. This relative movement of sheath and housing may for example be a linear sliding movement or a spiral movement, as more particularly exemplified hereinafter in FIGS. 3A and 3B of the drawings.

Such relative movement of sheath and housing may be determined by one or more linear or spiral grooves or channels in the housing engaging one or more lugs or other projections on the sheath—or grooves or channels in the sheath engaging projections on the housing.

In the second position of the sheath, in which the needle is encapsulated, the sheath is retained against further movement relative to the needle. That retaining of the sheath is preferably irreversible or reversible only with difficulty. For example, one or more lugs or other projections on one of the relatively movable components may engage one or more apertures or slots in the other component, preferably under the pressure of a natural resilience in at least one of the components or under pressure from one or more springs.

The sheath may advantageously and conveniently be made from a resilient plastics material, for example polypropylene, and the housing may be made from the same, or a similar, material.

The invention will now be further described with reference to the accompanying drawings, wherein.

Figures 1A, 1B:
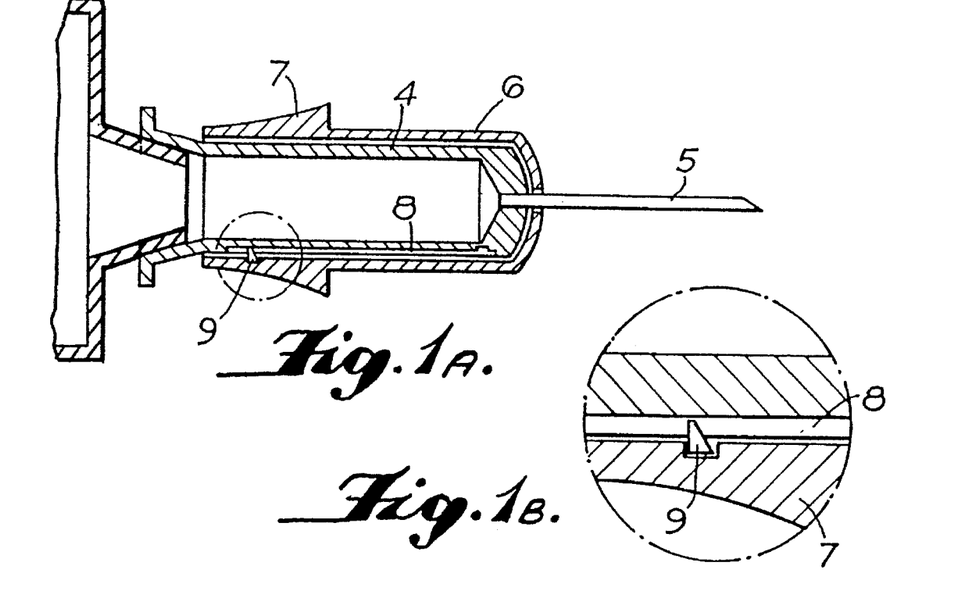
FIG. 1A is a sectional view of a first embodiment of the safety device according to the present invention, in a position in which the needle may be used normally.
FIG. 1B is an enlarged detailed view of the circled portion of FIG. 1A.

The embodiment of the invention shown in FIGS. 1A and 1B comprises a needle housing 4 in the form of a plastics moulding carrying a needle 5 and, slidably supported upon the housing 4, a plastics sheath 6 incorporating a thumb-guard 7 integral therewith. Also incorporated in the housing 4 and running lengthwise, is a channel 8. The sheath 6 incorporates a self-springed spigot 9 which slides alone the channel 8, as shown in more detail in the enlarged inset. When the sheath travels to the end of the channel 8, the self-springed spigot 9 drops into a small "well" 10, thus locking the sliding sheath in position. The length of the sheath is such that, when it is locked in position, the sharp end of the needle is completely enclosed by the sheath, as shown in FIG. 1B.

The housing 4 is designed to mate with any standard syringe barrel or luer connector. After use, the protective sheath is extended into the locked position, thus encapsulating the needle in a safe manner.

Figures 2A, 2B:
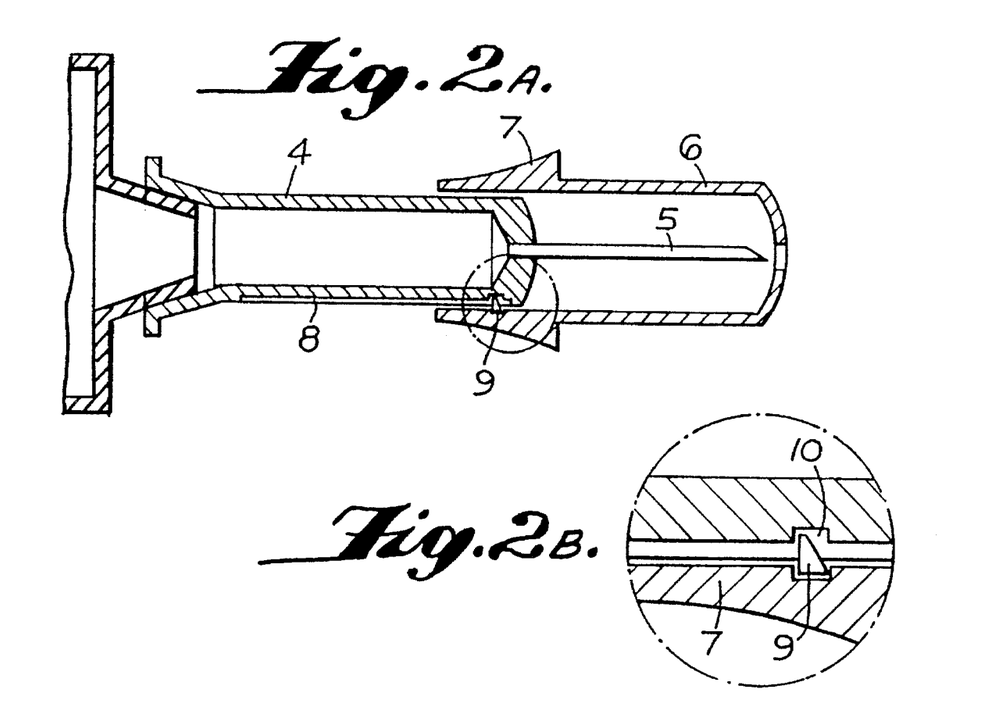
FIG. 2A is a view corresponding to that of FIG. 1A but with the sheath moved to encapsulate the needle.
FIG. 2B is an enlarged detailed view of the circled portion of FIG. 2A.

The embodiment of the invention shown in FIGS. 2A to 2C is designed to allow encapsulation of a hypodermic needle 21 which is tethered to a syringe (not shown) by an extension tube 22. The needle 21 is sandwiched between two plastics mouldings or pressings 23,24 which together form a sheath 25. A part 26 of the sheath 25 is permanently attached to the hypodermic needle. At points 23a and 24a the plastic is formed in a manner which allows the free ends of members 23 and 24 to hinge as indicated. Near to its outer end, the member 23 carries two spigots 27, which are designed to mate with holes 28 in the member 24 (when the sheath is in its folded position) and lock the sheath securely around the needle 21.

Figures 3, 4A, 4B:
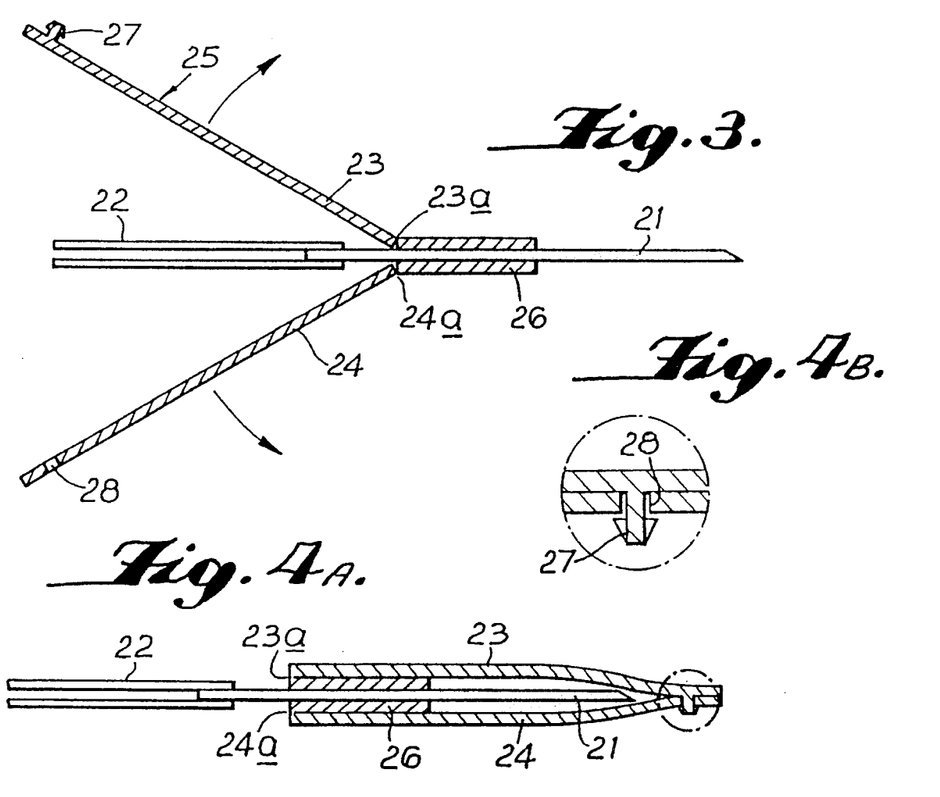
FIG. 3 is a sectional view of a second embodiment of the safety device according to the present invention, in a position in which the needle may be used normally.
FIG. 4A is a view corresponding to that of FIG. 3 but with the sheath folded to encapsulate the needle.
FIG. 4B is an enlarged view of the circled portion of FIG. 4A.
Figure 4C:
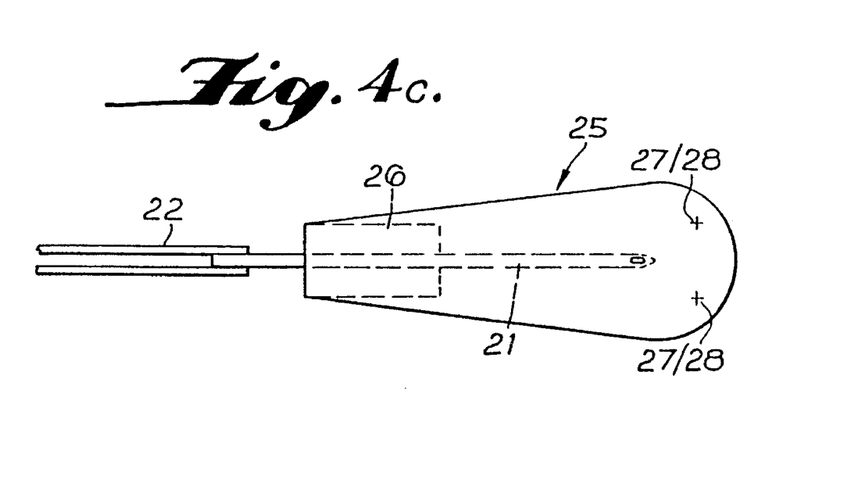
FIG. 4C is a plan view of the device in the position shown in FIG. 4A.
Figure 5A:
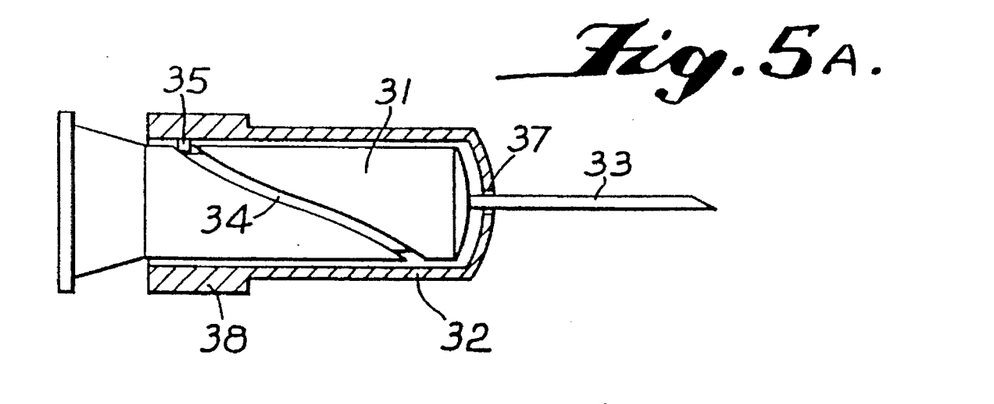
FIG. 5A is a view, partly in section of a third embodiment of the safety device according to the present invention, in a position in which the needle may be used normally.
Figure 5B:
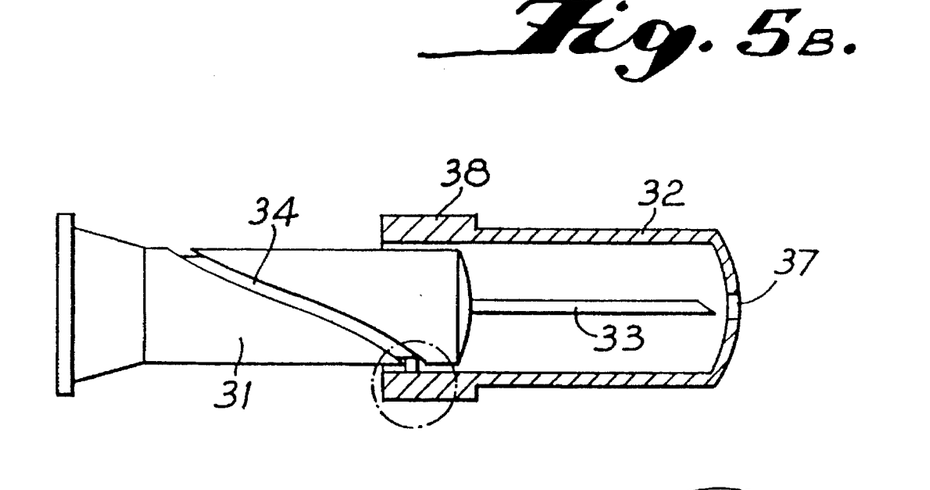
FIG. 5B is a view corresponding to that of FIG. 5A but with the sheath moved to encapsulate the needle.
Figure 5C:
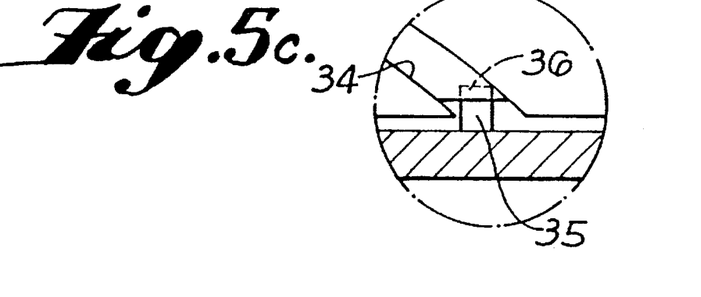
FIG. 5C is an enlarged view of the circled portion of FIG. 5B.

The third embodiment of the invention, as illustrated in FIGS. 3A and 3B, comprises a needle housing 31 in the form of a plastics moulding, a plastics sheath 32 which is free to rotate thereon and a needle 33. Impressed into the housing 31 is a helical groove 34 extending from near the end of the housing 31 which is distal to the needle 33 towards the needle. The sheath 32 has a self-springed spigot 35 which fits into, and is free to move along, the helical groove 34. As shown in FIG. 3B, rotation of the sheath 32 in a clockwise direction (viewed from the rear) will result in a forward motion causing the sheath to encapsulate the needle 33. At the end of its travel the springed spigot 35 drops into a "well" 36 thereby locking the sheath in position. The length of the sheath 32 is such that when it has reached this locked position the needle is completely encapsulated and withdrawn beyond the orifice 37 in the outer end of the sheath.

The device shown in FIGS. 3A and 3B is designed to mate with any standard syringe barrel or luer connector. After use, the protective sheath is placed in position by applying a twisting force to the sheath. To facilitate the application of this twisting force, a raised section 38 may be incorporated into the sheath's surface.

This form of the invention may be fabricated with one or more helical grooves, which may extend in a clockwise or anti-clockwise direction. For greater mechanical strength and stability, a double helix may be preferred.

We claim:

1. For use with clinical apparatus operably applicable to a patient by way of a deliberate skin puncture, a needle assembly operable to effect said skin puncture and comprising:

a support structure having a first end region;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a stop mechanism effective to constrain said guard from movement towards and around the apparatus when in place, which mechanism is located in said first end region of said support structure.

2. An assembly according to claim 1 wherein said support structure first end region is remote from said needle opposite end portion.

3. Clinical apparatus operably applicable to a patient by way of a skin puncture, comprising:

an elongate body defining a longitudinal passageway therethrough for transfer of fluid relative to a patient, and having a first connector formation at one end thereof, said formation including a first abutment surface extending transversely of said passageway;

in combination with:

a disposable non-reusable needle assembly operable to effect said skin puncture and comprising:

a needle support structure;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a sheath surrounding said needle and mounted directly on said sub-assembly for relative movement in the longitudinal direction of said needle from a first position in which said needle tip portion is exposed to effect said puncture, to a second position in which said needle tip portion is enclosed within said sheath;

a locking mechanism including first and second elements, said first element being a projection extending from said sheath, said second element being a stop surface defining a recess in said housing, said elements each extending transversely of said needle longitudinal direction, said elements being spaced apart in said longitudinal direction when said guard is in said first position, said projection being subject to a bias force acting between said housing and sheath during said relative movement, and said projection being automatically irreversibly moved into said recess alongside said stop surface in response to said bias force when said sheath is in said second position to inhibit a returning relative movement thereof towards said first position; and a second connector formation at one end of said needle assembly, said second connector formation including a second abutment surface extending transversely of said needle longitudinal direction;

said apparatus and assembly being separably interconnected for use by way of said first and second connector formation, with said first and second abutment surfaces mutually engaged and effective to constrain said sheath from movement towards and around said apparatus.

4. Clinical apparatus operably applicable to a patient by way of a skin puncture, comprising:

an elongate body defining a longitudinal passageway therethrough for transfer of fluid relative to a patient, and having a first connector formation at one end thereof, said formation including a first abutment surface extending transversely of said passageway;

in combination with:

a disposable non-reusable needle assembly operable to effect said skin puncture and comprising:

a needle support structure;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a sheath surrounding said needle and mounted directly on said sub-assembly for relative movement in the longitudinal direction of said needle from a first position in which said needle tip portion is exposed to effect said puncture, to a second position in which said needle tip portion is enclosed within said sheath;

a locking mechanism including first and second elements, said first element being a projection from one of said structure and sheath, said second element being a stop surface defining a recess in the other of said structure and sheath, said elements each extending transversely of said needle longitudinal direction, said elements being spaced apart in said longitudinal direction when said guard is in said first position, said projection being subject to a bias force acting between said structure and sheath during said relative movement, and said projection being automatically irreversibly moved into said recess alongside said stop surface in response to said bias force when said sheath is in said second position to inhibit a returning relative movement thereof towards said first position; and a second connector formation at one end of said needle support structure, said second connector formation including a second abutment surface extending transversely of said needle longitudinal direction;

said apparatus and assembly being separably interconnected for use by way of said first and second connector formation, with said first and second abutment surfaces mutually engaged and effective to constrain said sheath from movement towards and around said apparatus.

5. Clinical apparatus operably applicable to a patient by way of a skin puncture, comprising:

an elongate body defining a longitudinal passageway therethrough for transfer of fluid relative to a patient, and having a first connector formation at one end thereof, said formation including a first abutment surface extending transversely of said passageway;

in combination with:

a disposable non-reusable needle assembly operable to effect said skin puncture and comprising:

a needle support structure;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a sheath surrounding said needle and mounted directly on said sub-assembly for relative movement in the longitudinal direction of said needle from a first position in which said needle tip portion is exposed to effect said puncture, to a second position in which said needle tip portion is enclosed within said sheath;

a locking mechanism including first and second elements, said first element being a projection from one of said structure and sheath, said second element being a stop surface defining a recess in the other of said structure and sheath, said elements each extending transversely of said needle longitudinal direction, said elements being spaced apart in said longitudinal direction when said guard is in said first position, said projection being subject to a bias force acting between said housing and sheath during said relative movement, and said projection being automatically irreversibly moved into said recess alongside said stop surface in response to said bias force when said sheath is in said second position to inhibit a returning relative movement thereof towards said first position; and a second connector formation at one end of said needle assembly, said second connector formation including a second abutment surface extending transversely of said needle longitudinal direction;

said apparatus and assembly being separably interconnected for use by way of said first and second connector formation, with said first and second abutment surfaces mutually engaged and effective to constrain said sheath from movement towards and around said apparatus, the combination being such that when said apparatus and assembly are interconnected for use, said passageway and needle are communicated for fluid flow serially therethrough.

6. A combination according to claim 5 wherein said apparatus comprises a syringe.

7. Clinical apparatus in combination with a needle assembly, said apparatus being operably applicable to a patient by way of a deliberate skin puncture, and said needle assembly being operable to effect said skin puncture, wherein said apparatus comprises:
an elongate body defining a longitudinal passageway therethrough for transfer of fluid relative to a patient, and having a first connector formation at one end thereof, said formation including a first abutment surface extending transversely of said passageway;

said needle assembly comprises:
a support structure;
a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;
a guard mounted directly on said sub-assembly for movement relative thereto in the longitudinal direction of said needle from a first position in which said tip is exposed to effect said deliberate puncture, to a second position in which said tip is embraced by said guard to prevent unintended skin puncture;
a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and
a second connector formation at one end of said needle assembly, said second connector formation including a second abutment surface extending traversely of said needle longitudinal direction; and
said apparatus and assembly being separably interconnected for use by way of said first and second connector formations, with said apparatus held outside said needle, and with said first and second abutment surfaces mutually engaged and effective to constrain said guard from movement towards and around said apparatus.

8. A combination according to claim 7 wherein said guard is mounted directly on said support structure.

9. A combination according to claim 8 wherein said guard comprises a sheath which is dimensioned such that, when in said second position, it embraces the whole length of said needle projecting from said structure.

10. Clinical apparatus in combination with a needle assembly, said apparatus being operably applicable to a patient by way of a deliberate skin puncture, and said needle assembly being operable to effect said skin puncture, wherein said apparatus comprises:
an elongate body defining a longitudinal passageway therethrough for transfer of fluid relative to a patient, and having a first connector formation at one end thereof, said formation including a first abutment surface extending transversely of said passageway;

said assembly comprises:
a support structure;
a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;
a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;
a locking mechanism including first and second elements, said first element being a projection from said guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and
a second connector formation at one end of said needle assembly, said second connector formation including a second abutment surface extending traversely of said needle longitudinal direction; and
said apparatus and assembly being separably interconnected for use by way of said first and second connector formations, with said apparatus held outside said needle, and with said first and second abutment surfaces mutually engaged and effective to constrain said guard from movement towards and around said apparatus.

11. A combination according to claim 10 wherein said locking mechanism second element stop surface defines said space as a recess in said support structure.

12. Clinical apparatus in combination with a needle assembly, said apparatus being operably applicable to a patient by way of a deliberate skin puncture, and said needle assembly being operable to effect said skin puncture, wherein said apparatus comprises:
an elongate body defining a longitudinal passageway therethrough for transfer of fluid relative to a patient, and having a first connector formation at one end thereof, said formation including a first abutment surface extending transversely of said passageway;

said assembly comprises:
a support structure;
a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;
a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;
a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and
a second connector formation at one end of said needle assembly, said second connector formation including a second abutment surface extending traversely of said needle longitudinal direction; and
said apparatus and assembly being separably interconnected for use by way of said first and second connector formations, with said apparatus held outside said needle, and with said first and second abutment surfaces mutually engaged and effective to constrain said guard from movement towards and around said apparatus,
and wherein said locking mechanism second element stop surface defines said space as a recess in the other of said sub-assembly and guard.

13. Clinical apparatus in combination with a needle assembly, said apparatus being operably applicable to a patient by way of a deliberate skin puncture, and said needle assembly being operable to effect said skin puncture, wherein said apparatus comprises:
an elongate body defining a longitudinal passageway therethrough for transfer of fluid relative to a patient, and having a first connector formation at one end thereof, said formation including a first abutment surface extending transversely of said passageway;

said assembly comprises:
a support structure;
a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;
a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;
a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and
a second connector formation at one end of said needle assembly, said second connector formation including a second abutment surface extending traversely of said needle longitudinal direction; and
said apparatus and assembly being separably interconnected for use by way of said first and second connector formations, with said apparatus held outside said needle, and with said first and second abutment surfaces mutually engaged and effective to constrain said guard from movement towards and around said apparatus,
and wherein said second connector formation is at one end of said support structure.

14. Clinical apparatus in combination with a needle assembly, said apparatus being operably applicable to a patient by way of a deliberate skin puncture, and said needle assembly being operable to effect said skin puncture, wherein said apparatus comprises:
an elongate body defining a longitudinal passageway therethrough for transfer of fluid relative to a patient, and having a first connector formation at one end thereof, said formation including a first abutment surface extending transversely of said passageway;

said assembly comprises:
a support structure;
a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a second connector formation at one end of said needle assembly, said second connector formation including a second abutment surface extending traversely of said needle longitudinal direction; and said apparatus and assembly being separably interconnected for use by way of said first and second connector formations, with said apparatus held outside said needle, and with said first and second abutment surfaces mutually engaged and effective to constrain said guard from movement towards and around said apparatus.

15. A combination according to claim 14 wherein, when said apparatus and assembly are interconnected for use, said passageway and needle are communicated for fluid flow serially therethrough.

16. A combination according to claim 15 wherein said apparatus comprises a syringe.

17. For use with clinical apparatus operably applicable to a patient by way of a deliberate skin puncture, a needle assembly operable to effect said skin puncture and comprising:

a support structure;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a stop mechanism effective to constrain said guard from movement towards and around the apparatus when in place, and wherein said guard is mounted directly on said support structure.

18. For use with clinical apparatus operably applicable to a patient by way of a deliberate skin puncture, a needle assembly operable to effect said skin puncture and comprising:

a support structure;

a needle having one end portion fixedly mounted in said structure to form therewith a sub-assembly and an opposite end portion of said needle projecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a stop mechanism effective to constrain said guard from movement towards and around the apparatus when in place, and wherein said guard comprises a sheath which is dimensioned such that, when in said second position, it embraces the whole length of said needle opposite end portion projecting from said structure.

19. For use with clinical apparatus operably applicable to a patient by way of a deliberate skin puncture, a needle assembly operable to effect said skin puncture and comprising:

a support structure;

a needle having one end portion fixedly mounted in said structure to form therewith a sub-assembly and an opposite end portion of said needle protecting from said structure to terminate in a skin-puncturing tip having an opening therein, the needle being longitudinally hollowed to provide a direct fluid flow pathway extending therethrough between said opening which is in said tip and the remainder of the needle from said one end portion, the needle having no obstruction therein along the entire length of said pathway so that direct fluid flow along the entire length of the pathway is permitted;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from said guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a stop mechanism effective to constrain said guard from movement towards and around the apparatus when in place.

20. An assembly according to claim 19 wherein said locking mechanism second element stop surface defines said space as a recess in said support structure.

* * * * *